US008658692B2

(12) United States Patent
Kim et al.

(10) Patent No.: US 8,658,692 B2
(45) Date of Patent: Feb. 25, 2014

(54) METHOD OF PREPARATION AN INCLUSION-COMPLEX COMPRISING HYDROPHOBIC PHYSIOLOGICAL ACTIVATION MATERIAL INCLUDING WITH CYCLODEXTRIN AND ITS USE

(75) Inventors: Moo-Sung Kim, Suwon-si (KR); Sang-Rin Lee, Seoul (KR); Yong-Dae Park, Cheongju-si (KR)

(73) Assignee: Macrocare Tech., Ltd. (KR)

( * ) Notice: Subject to any disclaimer, the term of this patent is extended or adjusted under 35 U.S.C. 154(b) by 469 days.

(21) Appl. No.: 12/674,853

(22) PCT Filed: Sep. 3, 2008

(86) PCT No.: PCT/KR2008/005181
§ 371 (c)(1),
(2), (4) Date: Feb. 23, 2010

(87) PCT Pub. No.: WO2009/031809
PCT Pub. Date: Mar. 12, 2009

(65) Prior Publication Data
US 2011/0281940 A1      Nov. 17, 2011

(30) Foreign Application Priority Data

Sep. 5, 2007   (KR) .................. 10-2007-0090012

(51) Int. Cl.
*A01N 43/16* (2006.01)
(52) U.S. Cl.
USPC .......................................... 514/456; 514/778
(58) Field of Classification Search
USPC .......................... 514/58, 456, 778
See application file for complete search history.

(56) References Cited

U.S. PATENT DOCUMENTS

| | | | |
|---|---|---|---|
| 4,826,963 A * | 5/1989 | Stadler nee Szoke et al. | 536/103 |
| 5,376,645 A | 12/1994 | Stella et al. | |
| 5,847,108 A | 12/1998 | Kanaoka et al. | |
| 6,287,603 B1 * | 9/2001 | Prasad et al. | 424/489 |
| 2002/0025946 A1 * | 2/2002 | Buchanan et al. | 514/58 |

FOREIGN PATENT DOCUMENTS

| | | |
|---|---|---|
| JP | 09-309902 | 12/1997 |
| JP | 10-298175 | 11/1998 |
| JP | 2002-155072 | 5/2002 |
| KR | 10-2004-0009776 | 1/2004 |
| KR | 10-2005-0011889 | 1/2005 |
| KR | 10-2005-0039328 | 4/2005 |
| KR | 10-2006-0119384 | 11/2006 |
| KR | 10-2007-0002133 | 1/2007 |
| KR | 10-2007-0014672 | 2/2007 |
| WO | 2004/103380 | 12/2004 |

OTHER PUBLICATIONS

International Search Report—PCT/KR2008/005181 dated Feb. 16, 2009.
Written Opinion—PCT/KR2008/005181 dated Feb. 16, 2009.

* cited by examiner

*Primary Examiner* — Jason M Sims
*Assistant Examiner* — Ibrahim D Bori
(74) *Attorney, Agent, or Firm* — Cantor Colburn LLP

(57) ABSTRACT

Disclosed herein are a method for preparation of an inclusion-complex including a physiologically active hydrophobic substance in cyclodextrin and a derivative thereof, and use of the inclusion-complex prepared by the same. More particularly, the present invention provides a method for preparing an inclusion-complex, which includes agitating cyclodextrin and a derivative thereof in an agitator at high speed, spraying a physiologically active hydrophobic substance dissolved in alcohol onto the agitator, and drying and crushing the mixture obtained from the preceding step and, in addition, use of the prepared inclusion-complex. The present inventive method has merits of reduced inclusion time and increased inclusion rate. The prepared inclusion-complex has excellent cell and collagen proliferation effects compared to physiologically active hydrophobic substances which were not inclusion processed, thereby being used in production of a cosmetic composition with improved anti-wrinkle and anti-ageing effects.

9 Claims, 3 Drawing Sheets

METHOD OF PREPARATION AN INCLUSION-COMPLEX COMPRISING HYDROPHOBIC PHYSIOLOGICAL ACTIVATION MATERIAL INCLUDING WITH CYCLODEXTRIN AND ITS USE

TECHNICAL FIELD

The present invention relates to a process of preparing an inclusion-complex comprising cyclodextrin and/or derivatives thereof inclusion-combined with physiologically active hydrophobic substances, as well as a cosmetic composition with excellent effects of cell and collagen proliferation compared to physiologically active hydrophobic materials alone, which includes the inclusion-complex described above, thereby accomplishing favorably improved anti-wrinkle and anti-ageing effects.

BACKGROUND ART

In recent years, as functional cosmetics and foods have increasingly drawn attention all over the world, a great deal of studies and investigation into development of improved functional substances using natural plants, animal extracts and the like have been conducted.

Genistein represented by the following formula 1 is one of isoflavones, which are compounds isolated from plants and vegetables, and is well known to exist in soy beans, *sophora japonica* L., clover and other plants:

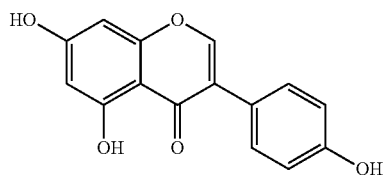

Formula 1

Such an isoflavone is typically presented in a glycoside form that has a β-glycoside bonded thereto and/or an aglycone form that does not have a glucose moiety.

Isoflavone glycosides are normally converted into the aglycone form by β-glycosides during digestion thereof. Isoflavone aglycones may include genistein, daidzein, glycitein and the like while isoflavone glycosides may include genistin, diadzein, glyzitin, and so forth.

Especially, isoflavones contained in soy beans may be mostly illustrated by genistin, 6-O-acetyl genistin, 6-O-malonyl genistin, etc., while fruits of *sophora japonica* L., may contain genistin represented by the following formula 2 as a genistein glycoside and, in addition, a sophoricoside represented by the following formula 3. Likewise, other plants and/or vegetables may contain a variety of genisteins and glycosides thereof.

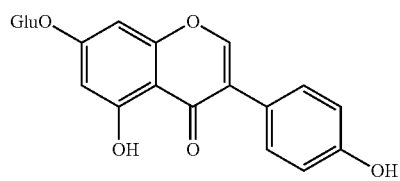

Formula 2

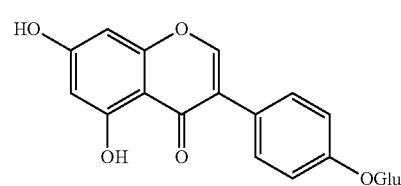

Formula 3

[Sophoricoside]
In the above formulae 2 and 3, Glu is

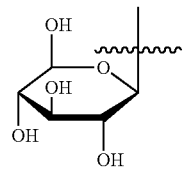

A number of animal experiments and human experiments report that genistein exhibits excellent effects of lowering cholesterol levels and inhibiting generation of adipose tissue. It was also disclosed that genistein is effective in protection and treatment of various cancers ROI as breast cancer, prostate cancer, skin cancer, colon cancer and the like, and may reduce or prevent a variety of menopausal symptoms including, for example, osteoporosis. Accordingly, among isolflavones, genistein is the most greatly studied in view of mechanism and safety.

Korean Patent No. 10-0500641 disclosed a hair, composition containing genistein with excellent hair growth promotion effects and/or hair loss prevention effects.

International Patent Application No. PCT/JP2004/006726 also described various applications of an isoflavone composition such as cosmetics, foods, medicines, etc.

Korean Laid-Open Application No. 2005-11889 proposed a transdermal drug composition including genistein for protection of intercellular information delivery performance and, especially, explained skin ageing protection effects of the composition.

Korean Laid-Open Application No. 2007-14672 disclosed a transdermal drug composition containing genistein or daidzein, characterized by inhibiting phagocytosis of dermal keratinocytes and efficiently reducing movement of melanosome from melanocytes into keratinocytes.

Additionally, Korean Laid-Open Application No. 2007-2133 described that a combination of palmitoyl pentapeptide, soy bean germ isoflavone aglycone, alfalfa extract and iris extract improves anti-wrinkle effects and enhances skin resilience.

Isoflavone or genistein mentioned in the above documents often refers to a simple extract directly obtained from soy beans or other plants and/or vegetables. However, it is generally known that isoflavones are minimally soluble in water, thereby inhibiting application thereof to beverages and simple liquid products. Technologies from abroad in regard to water soluble isoflavones have recently been disclosed, including, for example, Japanese Patent No. 10,298,175 and U.S. Pat. No. 5,847,108 owned by FUJICCO Co. Ltd., describing a process for preparation of a water-solubilized isoflavone by an inclusion method using beta-cyclodextrin.

FUJICCO's patents suggested a kneading method including continuous and slow reaction of isoflavone having more than saturation concentration and cyclodextrin in a kneader.

However, the process described above requires at least 3 hours for inclusion and a rate of inclusion is not particularly high.

In particular, an inclusion process of a hydrophobic compound may mostly include a simple high agitation process, a process comprising dissolving a compound in an organic solvent and inclusion processing the mixture while evaporating, a kneading method conducted at saturation concentration or more, and the like.

Korean Laid-Open Application No. 2005-39328 describes a process for production of isoflavone from a combination wherein a cyclodextrin solution is added to an isoflavone containing plant to prodire an isoflavone-cyclodextrin combination, followed by extracting isoflavone from the combination using a coagulant.

Japanese Laid-Open Application No. 9-309902 discloses a method for preparation of an inclusion-complex wherein isoflavone and cyclodextrin are dissolved in water, heated and cooled so as to prodire an inclusion-complex which functions to inhibit bitterness.

As described above, there were attempts to conduct inclusion processing of isoflavone by inclusion performance of cyclodextrin. However, these processes have problems such as extended time for inclusion of isoflavone and inferior rate of inclusion.

DISCLOSURE OF INVENTION

Technical Problem

Accordingly, the present inventors developed a method for processing genistein to be included in hydroxypropyl β-cyclodextrin or cyclodextrin using a Henschel mixer so as to reduce inclusion time while improving a rate of inclusion, thereby enabling wide application of various physiologically active hydrophobic substances with different functions while enhancing economical advantages thereof. Such an inclusion-complex exhibited more excellent effects upon cell proliferation and collagen formation compared to genistein that was not inclusion processed.

An object of the present invention is to provide a method for preparation of an inclusion-complex comprising a physiologically active hydrophobic substance included in cyclodextrin and a derivative thereof.

Another object of the present invention is to provide a composition promoting excellent cell and collagen proliferation, which includes the inclusion-complex described above as an active ingredient.

A still further object of the present invention is to provide a cosmetic composition with excellent anti-wrinkle and anti-ageing effects, which includes the inclusion-complex described above as an active ingredient.

Technical Solution

Therefore, the present invention provides a method for preparation of an inclusion-complex comprising: agitating cyclodextrin and a derivative thereof in an agitator at high speed; spraying a physiologically active hydrophobic substance dissolved in alcohol onto the agitator; and drying and milling the mixture obtained from the preceding step.

The present invention also provides a composition for cell and collagen proliferation, comprising an inclusion-complex prepared by including a physiologically active hydrophobic substance in cyclodextrin and a derivative thereof.

In addition, the present invention provides a cosmetic composition with excellent anti-wrinkle and anti-ageing effects, comprising an inclusion-complex prepared by including a physiologically active hydrophobic substance in cyclodextrin and a derivative thereof.

Advantageous Effects

According to the present invention, a method for preparation of an inclusion-complex comprising a physiologically active hydrophobic substance included in hydroxypropyl β-cyclodextrin or cyclodextrin has merits of rapid processing and excellent inclusion effects, compared to conventional methods such as use of organic solvents, a kneading process, etc.

Such an inclusion-complex comprising the physiologically active hydrophobic substance exhibits superior cell and collagen proliferation over the physiologically active hydrophobic substance alone or other cyclodextrin inclusion-complexes, thus improving anti-wrinkle and anti-ageing effects.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Details of the above objects and other features of the present invention will be more clearly understood from the following detailed description with reference to the accompanying drawings.

Figure 1:
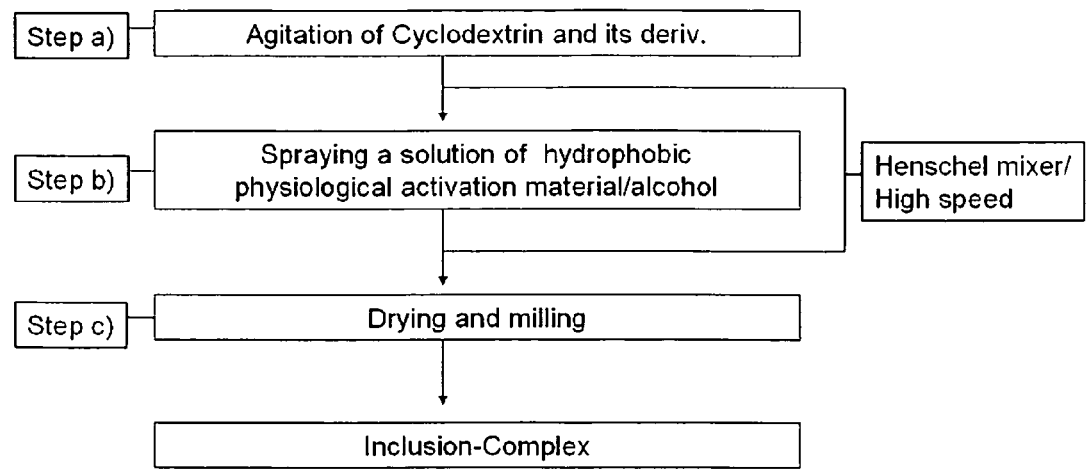
FIG. 1 is a flow chart illustrating the order of preparing an inclusion-complex according to the present invention.

FIG. 1 is a flow chart illustrating the order of preparing an inclusion-complex according to the present invention.

The inclusion-complex prepared according to the preparation order shown in FIG. 1 may have a structure wherein a physiologically active hydrophobic substance (sometimes, abbreviated to "active substance") is included in cyclodextrin and a derivative thereof. More particularly, the inclusion-complex may be prepared by a process comprising: (a) agitating cyclodextrin and a derivative thereof in an agitator at high speed; (b) spraying a physiologically active hydrophobic substance dissolved in alcohol onto the agitator; and (c) drying and milling the mixture obtained from the preceding step.

Firstly, in the step (a), cyclodextrin and a derivative thereof are agitated in an agitator at high speed.

Such cyclodextrin has an annular doughnut structure wherein a hydrophobic pore is formed in a molecule of the cyclodextrin, while having hydrophilic properties around outer side of the molecule. Because of this specific structure, the cyclodextrin may recognize a variety of hydrophobic organic compounds in the inner pore so as to form an inclusion compound with excellent physical properties.

The cyclodextrin described above may include α-, β- and γ-cyclodextrins based on the number of glucose and, in addition, derivatives of cyclodextrin in order to solve insolubility and instability thereof.

Such cyclodextrin derivatives may include, for example: hydroxyalkyl cyclodextrin such as hydroxymethyl cyclodextrin, hydroxyethyl cyclodextrin, hydroxypropyl β-cyclodextrin and hydroxybutyl cyclodextrin; carboxyalkyl cyclodextrin such as carboxymethyl cyclodextrin, carboxyethyl cyclodextrin, carboxypropyl cyclodextrin and carboxybutyl cyclodextrin; methylcarboxymethyl cyclodextrin; amino cyclodextrin; and/or mixtures thereof.

The cyclodextrin derivatives may also include a branched cyclodextrin having 1 to several glucose molecules bonded thereto, a polymer type cyclodextrin formed by combining several cyclodextrins, and so forth.

From practical experiments, the present inventors found that using each of beta-cyclodextrin and hydroxylpropyl beta-cyclodextrin may achieve a relatively high rate of inclusion.

Especially, the present inventors demonstrated that the inclusion rate of the active substance is improved while reducing an inclusion time by adopting a Henschel mixer to agitate cyclodextrin so as to conduct inclusion of the active substance.

The Henschel mixer is generally used to blend powders. According to the present invention, cyclodextrin and a derivative thereof are added to the Henschel mixer and homogeneously mixed by agitating the same at a high speed ranging from 800 to 2,000 ppm, preferably, 1,500 to 1,800 ppm.

Next, in the step (b), the active substance in alcohol is spray added to the agitator.

The active substance may include, for example: genistein; genistin; daidzein; daidzin; glwitein; glycitin; and isoflavones or flavonoids containing the same, etc.

Genistein is represented by the following formula 1. Genistein may include, for example, extracts obtained from *sophora japonica* L. fruits or branches, soy beans, soy bean sprouts, clovers, licorices, alfalfas, pomegranates, flax seeds and the like, however, the present invention is not particularly limited thereto.

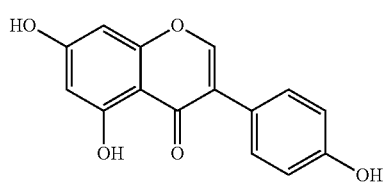

Formula 1

Genistin is represented by the following formula 2:

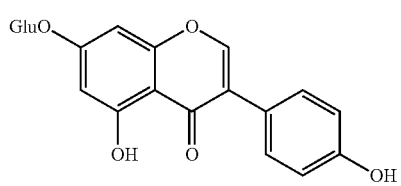

Formula 2

Daidzein refers to 7-hydroxy-3-(4-hydroxyphenyl)chromen-4-one and is represented by the following formula 4:

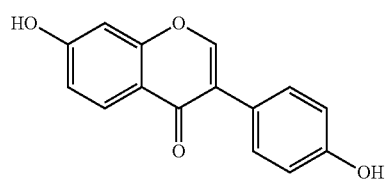

Formula 4

Daidzin refers to 7-(D-glucopyranoxyloxy)-3-(4-hydroxyphenyl)-4H-benzopyran-4-one and is represented by the following formula 5:

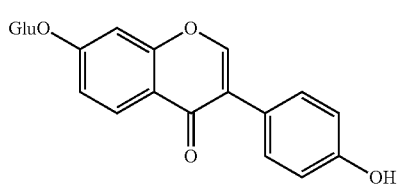

Formula 5

Glycitein refers to 4',7-dihydroxy-6-methoxyisoflavone and is represented by the following formula 6:

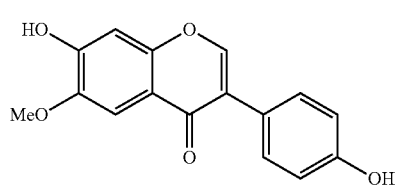

Formula 6

Glycitein refers to 3-(4-hydroxyphenyl)-6-methoxy-7-(3,4,5-trihydroxy-6-hydroxymethyltetrahydropyran-2-yloxy)-chromen-4-on and is represented by the following formula 7:

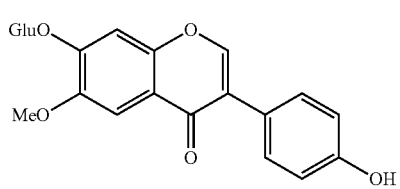

Formula 7

In formulae 2, 5 and 7, Glu is

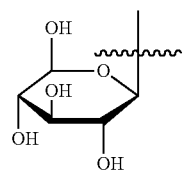

The alcohol solvent used herein may include a lower alcohol having 1 to 4 carbon atoms, preferably, at least one selected from a group consisting of methanol, ethanol, propanol, butanol and mixtures thereof.

The physiological active hydrophobic substance used herein may be dissolved in alcohol and a content thereof may range from 1 to 10% by weight ("wt. %"), preferably, 3 to 7 wt. %. When the content of the active substance in alcohol is less than the above range, an inclusion rate may be reduced. If the content exceeds the above range, the active substance may not be dissolved in alcohol, instead precipitating, causing a problem in spraying the substance. Accordingly, the content of the active substance in alcohol is preferably regulated within the above range.

The active substance may be spray added in a weight ratio of 1/100 to 1/1, preferably, 1/50 to 1/3 relative to content of cyclodextrin and a derivative thereof. When the amount of the active substance to be spray added is less than the above range, the inclusion rate may be reduced. If the amount exceeds the above range, the unreacted substance portion, which was not inclusion processed, must be removed. Therefore, the amount of the active substance to be spray added is preferably regulated within the above range.

As for spray addition, a Henschel mixer containing cyclodextrin and a derivative thereof is operated to agitate the contents at the same speed as in the step (a), that is, a range of 800 to 2,000 rpm, preferably, 1,500 to 1,800 rpm. The inclusion time may range from 10 to 60 minutes. If the agitation speed or the inclusion time is less than the above range, the inclusion rate may be reduced. On the other hand, even when each of these conditions exceeds the above range, the inclusion rate is substantially not improved. Therefore, these conditions are preferably controlled within the above ranges.

Spraying the physiologically active hydrophobic substance under agitation at high speed, the active substance may be rapidly and homogeneously included in cyclodextrin and a derivative thereof.

Conventional methods for cyclodextrin inclusion mostly used in industrial applications may include, for example:

1) use of a homogenizer for high speed agitation in a water soluble solution when a relatively water-soluble substance undergoes inclusion processing;

2) a process for preparation of an inclusion-complex using an organic solvent wherein a slightly water-soluble substance is dissolved in the organic solvent swh as alcohol and the prepared solution is mixed with a cyclodextrin containing solution or is dropped into the cyclodextrin containing solution while evaporating the organic solvent;

3) a kneading process wherein a hydrophobic substance having more than saturation concentration is continuously and slowly reacted with cyclodextrin in a kneader, and so forth.

However, the use of the homogenizer has restriction in applications. More particularly, if the substance has poor water solubility, the homogenizer is minimally effective. The organic solvent method requires a large amount of organic solvent and extended time for evaporating the organic solvent. Lastly, the kneading method needs extended time for achieving desired effects.

For instance, U.S. Pat. No. 5,847,108 granted to FUJICCO Co., Ltd. described that the kneading method requires at least 30 minutes to 3 hours and much longer time for industrial mass-production.

Referring to Experimental Example 1 of the present invention, a process for including genistein in cyclodextrin was performed by each of methods including, use of a Henschel mixer, use of a homogenizer, an organic solvent method and a kneading method. As a result, it was found that using the Henschel mixer attained an inclusion rate of at least 20% after only 15 minutes. However, the other methods, that is, the use of the homogenizer, the organic solvent method and the kneading method required extended inclusion time and achieved a maximum inclusion rate of no more than 13.4%.

Next, in step (c), the prepared mixture was dried and milled to complete production of an inclusion-complex.

Drying the mixture removed an alcohol fraction. Such a drying may include, for example, hot air drying, vacuum drying, freeze-drying and fluidized bed drying. The drying is continued until the alcohol fraction is substantially eliminated. For example, hot air drying may be carried out at 50 to 100° C. for 1 to 10 hours.

Following this, the dried product was pulverized using a common mill to produce an inclusion-complex in a powder state.

The inclusion-complex resulting from all of the above sequential processes exhibited excellent cell and collagen proliferation, preferably being used as a composition for cell and collagen proliferation.

Referring to Experimental Example 2 of the present invention, cell proliferation performance of the inclusion-complex was determined in order to evaluate effects of the inclusion-complex. From the results, it was demonstrated that an inclusion-complex based on hydroxypropyl β-cyclodextrin/genistein has more excellent cell proliferation performance than genistein alone or an inclusion-complex based on β-cyclodextrin/genistein.

Referring to Experimental Example 3 of the present invention, compared to a fibroblast treated with vitamin C as a control, genistein exhibited more excellent effects with increased concentration. The β-cyclodextrin/genistein inclusion-complex prepared according to the present invention exhibited a maximum increase in collagen synthesis of 19%, while the fibroblast treated with hydroxypropyl β-cyclodextrin/genistein showed greater increase in collagen synthesis at a maximum of 34%.

Consequently, such an inclusion-complex with excellent cell and collagen proliferation effects is preferably applicable to production of a composition for enhancing anti-wrinkle and anti-ageing effects.

An amount of the inclusion-complex may range from 0.0001 to 10.0 wt. % of the total weight of the composition. If the amount is less than the above range, desired effects may not be achieved. On the other hand, even when the amount exceeds the above range, the effects of the composition may not be further enhanced.

A cosmetic composition according to the present invention may further include typical substances as well as the inclusion-complex described above as an active ingredient and, for example, common additives such as an antioxidant, a stabilizer, a dissolving agent, vitamins, a pigment and/or a fragrance and, in addition, a carrier.

The cosmetic composition of the present invention may be prepared in a variety of formulations including, for example, a solution, a suspension, an emulsion, a paste, a gel, a cream, a lotion, a powder, a soap, a surfactant containing a cleansing substance, an oil, a powder foundation, an emulsified foundation, a wax foundation, a spray and so forth, however, the present invention is not particularly restricted thereto. More preferably, the cosmetic composition may be prepared in the formulations such as a soft tonic water, a nutritional tonic water, a nutritional cream, a massage cream, an essence cream, an eye cream, a cleansing cream, a cleansing foam, cleansing water, a pack, a spray, a powder, etc.

If the formulation of the present invention is a paste, a cream or a gel, a carrier ingredient added to the formulation may be animal fat-based oil, vegetable-based oil, wax, paraffin, starch, tragacanth, cellulose derivatives, polyethyleneglycol, silicon, bentonite, silica, talc and/or zinc oxide.

If the formulation of the present invention is a powder or a spray, the carrier ingredient added to the formulation may be lactose, talc, silica, aluminum hydroxide, calcium silicate and/or a polyamide powder. In particular, if the formulation is a spray, the formulation may further include a propellant null as a chlorofluorohydrccarbon, propane/butane or dimethylether.

If the formulation of the present invention is a solution or emulsion, the carrier ingredient may be a solvent, a dissolving agent or an emulsifying agent, more particularly, may include water, ethanol, isopropanol, ethyl carbonate, ethyl acetate, benzyl alcohol, benzyl benzoate, propyleneglycol, 1,3-butylglycol oil, glycerol aliphatic ester, polyethyleneglyol, sorbitan fatty acid ester, etc.

If the formulation of the present invention is a suspension, the carrier ingredient may include: a liquid diluent such as water, ethanol and propyleneglycol; a suspending agent sigh as ethoxylated isostearyl alcohol, polyoxyethylene sorbitol ester and polyoxyethylene sorbitan ester; micro-crystalline cellulose; aluminum metahydroxide; bentonite; agar; tragacanth, and so forth.

If the formulation of the present invention is a surfactant containing cleaning substance, the carrier ingredient may include, for example, aliphatic alcohol sulfate, aliphatic alcohol ether sulfate, sulfostrcinic aid monoester, isoethionate, imidazolium derivatives, methyltaurate, sarcosinate, fatty acid amide ethersulfate, alkylamidobetain, aliphatic alcohol, fatty aid glyceride, fatty aid diethanolamide, vegetable-based oil, lanolin derivatives, ethoxylated glycerol fatty acid ester, and so forth.

Mode for the Invention

Hereinafter, preferred embodiments and examples of the present invention will be described in detail. However, these examples are given for the purpose of illustration and are not intended to limit the invention.

EXAMPLE 1

Preparation of an Inclusion-complex Containing Genistein in β-cyclodextrin Using a Henschel Mixer 4 kg of β-cyclodextrin was placed in a Henschel mixer and homogeneously agitated at 1500 rpm. After preparing a 5% genistein in ethanol solution, this solution was spray added to the agitated β-cyclodextrin, and then, reacted for 15 minutes. Herein, in order to determine a weight ratios of ingredients in the mixture, the reaction product was added to water after completing the reaction, and then heated at 100° C. The dissolved cyclodextrin and an inclusion-complex of genistein-cyclodextrin were filtered and the remaining unreacted genistein fraction was removed. Spray drying the filtered complex obtained a product in a powder form. After determining the weight ratios, a weight ratio at reaction of genistein :β-cyclodextrin was regulated to achieve a final weight ratio of 20:80. After that, this mixture was sunjected to hot air drying at 100° C. for 2 hours, followed by milling to produce an inclusion-complex in a powder form.

EXAMPLE 2

Preparation of an Inclusion-complex Containing Genistein in Hydroxypropyl β-cyclodextrin using a Henschel Mixer An inclusion-complex was produced by the same procedure as described in Example 1 except that hydroxypropyl (β-cyclodextrin was used in place of cyclodextrin.

COMPARATIVE EXAMPLE 1

Preparation of an Inclusion-complex Containing Genistein in Cyclodextrin Using a Homogenizer After adding 4 kg of cyclodextrin to 40 kg of ionized water and heating the solution at 90° C., 1 kg of genistein was added to the solution and reacted at the same temperature for 3 hours. After the reaction was completed, the dissolved cyclodextrin and an inclusion-complex of genistein-cyclodextrin were filtered and the remaining unreacted genistein fraction was removed. Spray drying the filtered complex obtained a product in a powder form.

COMPARATIVE EXAMPLE 2

Preparation of an Inclusion-complex Containing Genistein in Hydroxypropyl β-cyclodextrin Using a Homogenizer An inclusion-complex was produced by the same procedure as described in Comparative Example 1 except that hydroxypropyl β-cyclodextrin was used in place of cyclodextrin.

COMPARATIVE EXAMPLE 3

Preparation of an Inclusion-complex Containing Genistein in Cyclodextrin by an Organic Solvent Method 4 kg of cyclodextrin was placed in 40 kg of ionized water and heated at 90° C. Separately, genistein was added to ethanol to prepare a 5% genistein solution. 20 kg of the prepared genistein solution was dropped into the cyclodextrin solution at a rate of 1 kg per minute.

Following this, a reaction of the prepared mixture was carried out at 100° C. for 3 hours so as to evaporate the ethanol fraction. After completing the reaction, the dissolved cyclodextrin and an inclusion-complex of genistein-cyclodextrin were filtered and the remaining unreacted genistein fraction was removed. Spray drying the filtered complex obtained a prodirt in a powder form.

COMPARATIVE EXAMPLE 4

Preparation of an Inclusion-complex Containing Genistein in Hydroxypropyl β-cyclodextrin by an Organic Solvent Method An inclusion-complex was produced by the same procedure as described in Comparative Example 3 except that hydroxypropyl β-cyclodextrin was used in place of cyclodextrin.

COMPARATIVE EXAMPLE 5

Preparation of an Inclusion-complex Containing Genistein in Cyclodextrin by a Kneading Method After 4 kg of cyclodextrin was placed in 4 kg of ionized water and kneaded into a paste, the paste was placed in a kneader. Separately, genistein was added to ethanol to prepare a 50% genistein paste. 20 kg of the prepared genistein paste was added to the kneader, followed by continuously kneading the mixture for 6 hours.

Following this, the obtained paste was placed in 50 kg of water and heated at 100° C. The dissolved cyclodextrin and an inclusion-complex of genistein-cyclodextrin were filtered and the remaining unreacted genistein fraction was removed. Spray drying the filtered complex obtained a product in a powder form.

COMPARATIVE EXAMPLE 6

Preparation of an Inclusion-complex Containing Genistein in Hydroxypropyl β-cyclodextrin by a Kneading Method An inclusion-complex was produced by the same procedure as described in Comparative Example 5 except that hydroxypropyl β-cyclodextrin was used in place of cyclodextrin.

EXPERIMENTAL EXAMPLE 1

Determination of Inclusion Rate and Inclusion Time Dependent on Inclusion Methods Each of the inclusion-complexes produced from the examples and comparative examples described above was subjected to determination of inclusion rate and inclusion time. Results of the determination are shown in Table 1.

The inclusion rate was calculated by a process including: dissolving 0.1 g of an inclusion-complex obtained by an inclusion process in 100 ml of water; centrifuging the solution to remove the unreacted genistein fraction; measuring a content of genistein in the solution through HPLC. The used HPLC was a Mightysil RP-18 GP 250-4.6 (5 m) column with 15% acetonitrile solution. The inclusion-complex solution was poured into the HPLC at a flow rate of 1 ml/min for 40 minutes and analyzed at 254 nm using a detector.

for 4 hours. The obtained formazan was dissolved in dimethyl sulfoxide (DMSO). The formazan solution was subjected to determination of absorption at 570 nm using a microplate reader. The results are shown in Tables 2 and 3.

A: Cell Proliferation Effect of Genistein

Figure 2:
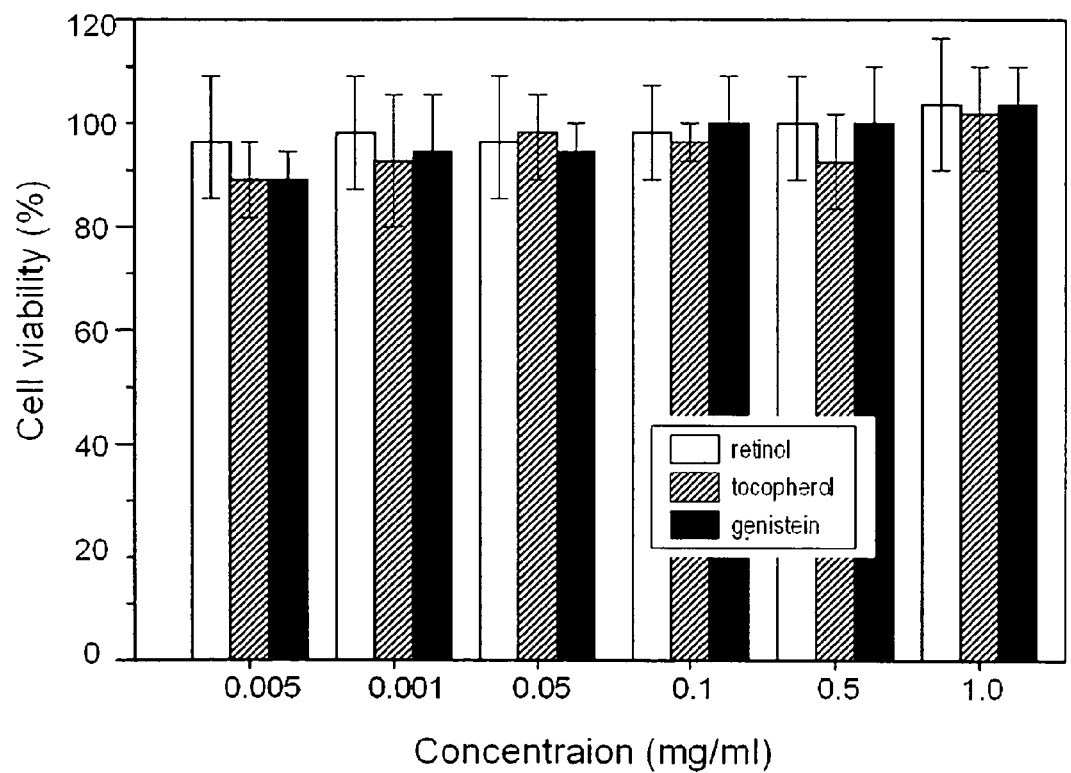
FIG. 2 depicts graphs illustrating cell viabilities dependent on concentrations of genistein, retinol and tocopherol.

FIG. 2 depicts graphs illustrating cell viabilities dependent on concentrations of genistein, retinol and tocopherol.

Referring to FIG. 2, as for each of genistein, retinol and tocopherol, cell viability was increased somewhat in proportion to concentration thereof.

B: Cell Proliferation Effect of Inclusion-Complex

Figure 3:
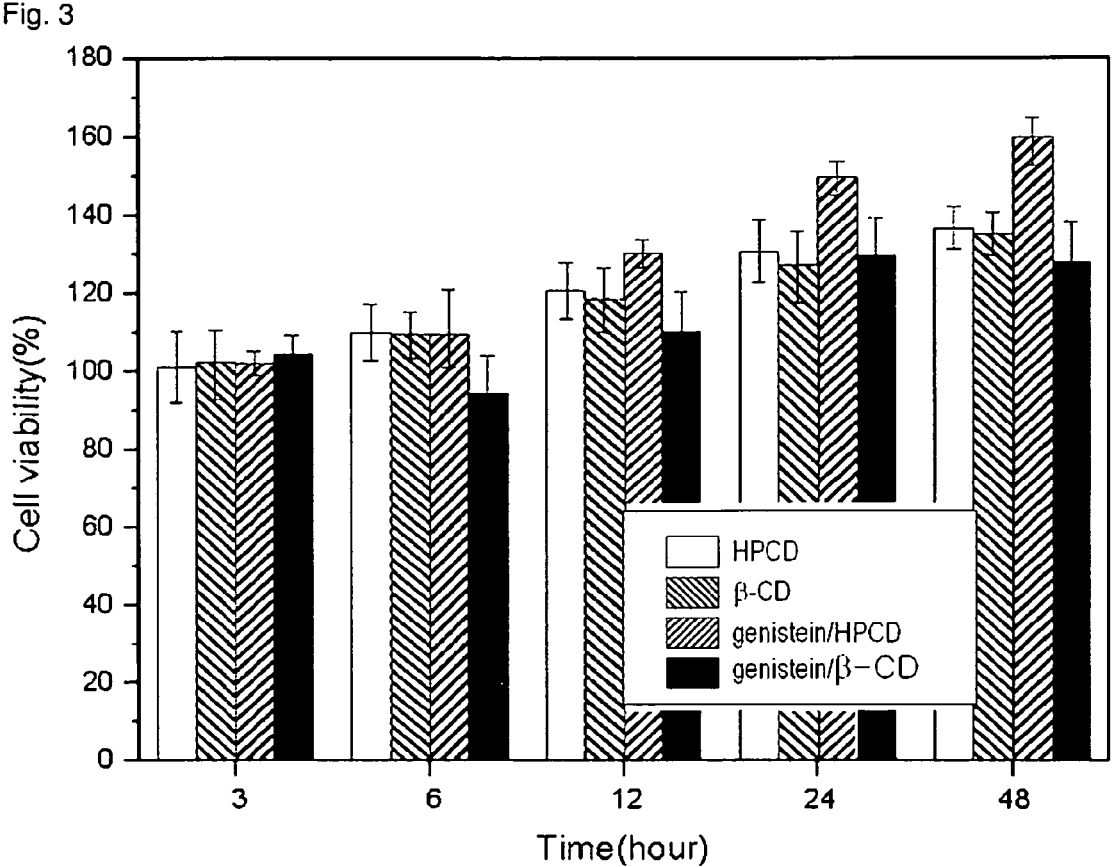
FIG. 3 depicts graphs illustrating cell viabilities of inclusion-complexes prepared in Examples 1 and 2 as well as hydroxypropyl β-cyclodextrin and β-cyclodextrin, respectively, depending on time.

FIG. 3 depicts graphs illustrating cell viabilities of the inclusion-complexes prepared in Examples 1 and 2 as well as hydroxypropyl β-cyclodextrin and β-cyclodextrin, respectively, depending on time.

Referring to FIG. 3, each of the inclusion-complexes prepared in Examples 1 and 2 exhibited superior cell viability and this fact means that these complexes have excellent cell proliferation performance. Especially, compared to the cell proliferation when genistein was used alone as shown in FIG. 2, the inclusion-complexes of the present invention exhibited considerably improved results.

In addition, as for the inclusion process of genisterin, it was observed that hydroxypropyl β-cyclodextrin exhibited more excellent cell proliferation than β-cyclodextrin. This result

TABLE 1

Inclusion rate and inclusion time of each inclusion method

| | Genistein/β-cyclodextrin | | | Genistein/hydroxypropyl β-cyclodextrin | |
|---|---|---|---|---|---|
| Section | Inclusion rate | Inclusion time | Section | Inclusion rate | Inclusion time |
| Example 1 | 22% | 15 minutes | Example 2 | 20.5% | 15 minutes |
| Comparative Example 1 | 1.2% | 3 hours | Comparative Example 2 | 3.1% | 3 hours |
| Comparative Example 3 | 8.2% | 3 hours | Comparative example 4 | 9.5% | 3 hours |
| Comparative Example 5 | 13.4% | 6 hours | Comparative example 6 | 10.4% | 6 hours |

EXPERIMENTAL EXAMPLE 2

Evaluation of Cell Proliferation Performance

In order to evaluate cell proliferation performance of the inclusion-complex according to the present invention, fibroblast proliferation performance was determined.

More particularly, human fibroblasts were cultured in Dulbecco s Modified Eagle's medium (DMEM) containing 2.5% fetal bovine serum (FBS) and the cultured cells were plated in a 96-well microtiter plate at 5,000 cells/well.

Each of the inclusion-complex produced in Example 1 (an inclusion-complex of β-cyclodextrin/geniste with a genistein concentration of 5%), the inclusion-complex produced in Example 2 (an inclusion-complex of hydroxypropyl β-cyclodextrin/genistein with a genistein concentration of 5%) was used as a test sample. On the other hand, genistein, retinol and tocopherol, hydroxypropyl β-cyclodextrin and β-cyclodextrin, respectively, were used as controls. Each of the samples was regulated to have a final concentration of 1 mg/ml and added to the fibroblasts, followed by additional culturing of the fibroblasts for 4 days.

After completing the culture, 50 μl of 0.2% MTT (3-[4,5-dimethylthiazol-2-yl]-2,5-diphenyltetrazolium bromide) solution was added to each well, and then, cultured at 37° C.

means that the inclusion-complex of hydroxyl β-cyclodextrin/genistein may alter stability or solubility of a substance and, in addition, may control functional efficiency of cells or bio-systems when the complex is applied to the cells or bio-systems owing to the features described above.

EXPERIMENTAL EXAMPLE 3

Evaluation of Collagen Proliferation Performance

In order to determine degree of collagen synthesis, human fibroblasts were cultured in a 24-well microtiter plate. The same sample as used for cell proliferation was diluted in a rate of 1/10 in a culture medium and the diluted sample was added to the cultured fibroblasts. The samples used herein were vitamin C, genistein, cyclodextrin, and the inclusion-complexes prepared in Examples 1 and 2.

At 3 days after culture, 0.5 ml of 10% FBS containing DMEM medium was added to each well, followed by adding 10 μCi of L[2,3,4,5-3H]-proline thereto. After 24 hours, the medium and the cells were collected from the well and fed into a 5% trichloroacetic acid (TCA) solution to rinse the product. The rinsed product was plated in two test tubes. 1 unit/μl of Type I collagenase was added to one of the test tubes and cultured at 37° C. for 90 minutes, while the other test tube was stored at 4° C.

After that, adding 0.05 ml of 50% TCA to both the test tubes and leaving the same at 4° C. for 20 minutes, each of the test tubes was subjected to centrifugation at 12,000 rpm for 10 minutes. The resultant supernatant and precipitate were detected using a liquid scintillation counter (LSC) to measure decay per minute (dpm) values. The measured dpm values were used to calculate relative collagen biosynthesis (RCB) values according to the following equation 1:

$$RCB = \text{collagen dpm value} / \{[(\text{total collagen collagen dpm value}) \times 5.4] + \text{collagen dpm value}\} \times 100 \quad \text{Equation 1}$$

TABLE 2

Collagen proliferation rate

| Test substance | Concentration | | |
|---|---|---|---|
| | $10^{-6}$ | $10^{-5}$ | $10^{-4}$ |
| β-cyclodextrin/genistein inclusion-complex (Example 1) | 106% | 116% | 117% |
| Hydroxypropyl β-cyclodextrin/genistein inclusion-complex (Example 2) | 111% | 131% | 134% |
| Vitamin C | 106% | 105% | 98% |
| Genistein | 105% | 112% | 115% |
| Cyclodextrin | 102% | 101% | 102% |
| Hydroxypropyl β-cyclodextrin | 101% | 104% | 104% |

Figure 4:
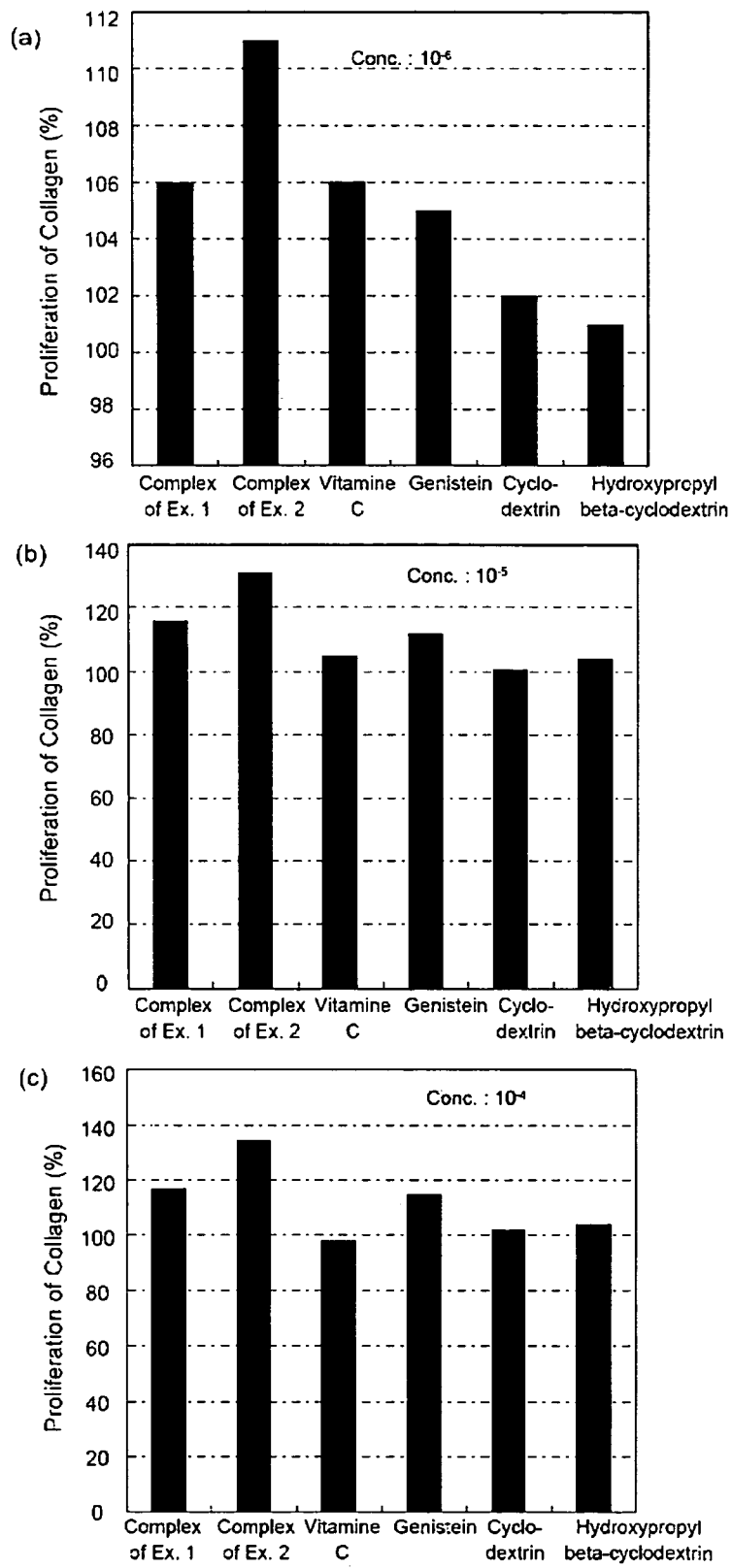
FIG. 4 depicts graphs illustrating collagen proliferation rates of various substances, in particular: an inclusion-complex comprising β-cyclodextrin/genistein (Example 1); another inclusion-complex comprising hydroxypropyl β-cyclodextrin/genistein (Example 2); vitamin C; genistein; cyclodextrin; and hydroxypropyl β-cyclodextrin, wherein the graph (a) exhibits the collagen proliferation rate when the substance has a concentration of $10^{-6}$, the graph (b) exhibits the collagen proliferation rate with the substance at $10^{-5}$, and the graph (c) exhibits the collagen proliferation rate with the substance at $10^{-4}$.

FIG. 4 depicts graphs illustrating the results of Table 2 and, in particular: the graph (a) exhibits the collagen proliferation rate when the substance has a concentration of $10^{-6}$; the graph (b) exhibits the collagen proliferation rate with the substance at $10^{-5}$; and the graph (c) exhibits the collagen proliferation rate with the substance at $10^{-4}$.

Referring to Table 2 and FIG. 4, it can be seen that the inclusion-complexes of the present invention prepared in Examples 1 and 2 exhibit higher collagen proliferation rates than others and the collagen proliferation may be improved with an increase in concentration of the inclusion-complex.

However, the collagen proliferation rate of vitamin C was decreased as its concentration increased. In addition, as for cyclodextrin or hydroxypropyl β-cyclodextrin, collagen proliferation was not greatly improved.

Hereinafter, preferred formulations of a cosmetic composition including a β-cyclodextrin/genistan inclusion-complex affording to the present invention will be described in greater detail in terms of constitutional ratios by weight thereof. However, the present inventive composition is not particularly limited thereto.

TABLE 3

Formulation Example 1: soft tonic water (skin lotion)

| Ingredients | wt. % |
|---|---|
| Inclusion-complex prepared in Example 2 | 1.0 |
| Glycerin | 3.0 |
| Butyleneglycol | 2.0 |
| Propyleneglycol | 2.0 |
| Carboxyvinyl polymer | 0.1 |
| PEG-12 nonylphenylether | 0.2 |
| Polysorbate 80 | 0.4 |
| Ethanol | 10.0 |
| Triethanolamine | 0.1 |
| Preservatives, colorings, perfumes | Proper amount |
| Purified water | To 100 |

TABLE 4

Formulation Example 3: nutritional tonic water (milk lotion)

| Ingredients | wt. % |
|---|---|
| Inclusion-complex prepared in Example 2 | 1.0 |
| Squalane | 4.0 |
| Wax | 4.0 |
| Polysorbate 60 | 1.5 |
| Sorbitan sesquiolate | 1.5 |
| Liquid paraffin | 0.5 |
| Caprylic/capric triglyceride | 5.0 |
| Glycerin | 3.0 |
| Butyleneglycol | 3.0 |
| Propyleneglycol | 3.0 |
| Carboxyvinyl polymer | 0.1 |
| Triethanolamine | 0.2 |
| Preservatives, colorings, perfumes | Proper amount |
| Purified water | To 100 |

TABLE 5

Formulation Example 3: nutritional cream

| Ingredients | wt. % |
|---|---|
| Inclusion-complex prepared in Example 2 | 1.0 |
| Wax | 10.0 |
| Polysorbate 60 | 1.5 |
| PEG 60 hydrogenated caster oil | 2.0 |
| Sorbitan sesquiolate | 0.5 |
| Liquid paraffin | 10.0 |
| squalane | 5.0 |
| Caprylic/capric triglyceride | 4.0 |
| glycerin | 5.0 |
| butyleneglycol | 3.0 |
| Propyleneglycol | 3.0 |
| Triethanolamine | 0.2 |
| Preservatives, colorings, perfumes | Proper amount |
| Purified water | To 100 |

TABLE 6

Formulation Example 4: massage cream

| Ingredients | wt. % |
|---|---|
| Inclusion-complex prepared in Example 2 | 1.0 |
| Wax | 10.0 |
| Polysorbate 60 | 1.5 |
| PEG 60 hydrogenated caster oil | 2.0 |
| Sorbitan sesquiolate | 0.8 |
| Liquid paraffin | 40.0 |
| Squalane | 4.0 |
| Caprylic/capric triglyceride | 4.0 |
| Glycerin | 5.0 |
| Butyleneglycol | 3.0 |
| Propyleneglycol | 3.0 |
| Triethanolamine | 0.2 |
| Preservatives, colorings, perfumes | Proper amount |
| Purified water | To 100 |

TABLE 7

Formulation Example 5: pack

| Ingredients | wt. % |
|---|---|
| Inclusion-complex prepared in Example 2 | 1.0 |
| Polyvinyl alcohol | 12.0 |
| Sodium carboxymethyl cellulose | 0.2 |
| Glycerin | 5.0 |
| Alantoin | 0.1 |
| Ethanol | 6.0 |

TABLE 7-continued

Formulation Example 5: pack

| Ingredients | wt. % |
| --- | --- |
| PEG-12 nonylphenylether | 0.3 |
| Polysorbate 60 | 0.3 |
| Preservatives, colorings, perfumes | Proper amount |
| Purified water | To 100 |

TABLE 8

Formulation Example 6: gel

| Ingredients | wt. % |
| --- | --- |
| Inclusion-complex prepared in Example 2 | 1.0 |
| Ethylenediamine acetic acid sodium | 0.05 |
| glycerin | 5.0 |
| Carboxylvinyl polymer | 0.3 |
| ethanol | 5.0 |
| PEG-60 hydrogenated caster oil | 0.5 |
| triethanolamine | 0.3 |
| Preservatives, colorings, perfumes | Proper amount |
| Purified water | To 100 |

Industrial Applicability

As will be apparent from the above, an inclusion-complex comprising a physiologically active hydrophobic substance in cyclodextrin and a derivative thereof according to the present invention is effectively used in preparation of a cosmetic composition with improved anti-wrinkle and anti-ageing effects.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for preparation of an inclusion-complex comprising a physiologically active hydrophobic substance in cyclodextrin or a derivative thereof, comprising:
   (a) agitating powdered cyclodextrin or a derivative thereof in an agitator at 800 to 2,000 rpm;
   (b) spraying a physiologically active hydrophobic substance dissolved in alcohol onto the powdered cyclodextrin or the derivative thereof in the agitator to form the inclusion-complex,
   wherein the physiologically active hydrophobic substance is sprayed while agitating the powdered cyclodextrin or the derivative thereof in the agitator; and
   (c) drying and milling the inclusion-complex obtained from the preceding step,
   wherein the cyclodextrin derivative is selected from a group consisting of a hydroxyalkyl cyclodextrin, a carboxyalkyl cyclodextrin, a branched cyclodextrin, a polymer type cyclodextrin formed by combining two or more cyclodextrins, and mixtures thereof.

2. The method according to claim 1, wherein cyclodextrin in the step (a) is at least one selected from a group consisting of α-cyclodextrin, β-cyclodextrin, γ-cyclodextrin and mixtures thereof, and the cyclodextrin derivative is at least one selected from a group consisting of: hydroxymethyl cyclodextrin, hydroxyethyl cyclodextrin, hydroxypropyl β-cyclodextrin and hydroxybutyl cyclodextrin; carboxymethyl cyclodextrin, carboxyethyl cyclodextrin, carboxypropyl cyclodextrin and carboxybutyl cyclodextrin; methylcarboxymethyl cyclodextrin; amino cyclodextrin; and mixtures thereof.

3. The method according to claim 1, wherein the agitation step (a) is performed using a Henschel mixer.

4. The method according to claim 1, wherein the physiologically active hydrophobic substance in the step (b) is at least one selected from a group consisting of genistein, genistin, daidzein, daidzin, glydtein, glycitin, and isoflavones, and flavonoids containing at least one of these substances.

5. The method according to claim 1, wherein the alcohol solvent in the step (b) is preferably at least one selected from a group consisting of methanol, ethanol, propanol, butanol and mixtures thereof.

6. The method according to claim 1, wherein the physiologically active hydrophobic substance in the step (b) is dissolved in an amount of 1 to 10 wt. % in alcohol.

7. The method according to claim 1, wherein the ratio of physiologically active hydrophobic substance to powered cyclodextrin or a derivative thereof in the inclusion complex is 1/100 to 1/1 relative to content of powdered cyclodextrin or a derivative thereof.

8. The method according to claim 1, wherein the drying step (c) is performed by hot air drying, vacuum drying, freeze drying or fluidized bed drying.

9. The method according to claim 1, wherein a time to form the inclusion complex ranges from 10 to 60 minutes.

* * * * *